United States Patent [19]

Hirano et al.

[11] Patent Number: 4,854,694

[45] Date of Patent: Aug. 8, 1989

[54] EYE FIXATION MONITOR

[75] Inventors: Takashi Hirano, Shiki; Atsushi Kojima, Hino, both of Japan

[73] Assignee: Kowa Company Limited, Japan

[21] Appl. No.: 59,736

[22] Filed: Jun. 8, 1987

[30] Foreign Application Priority Data

Jun. 6, 1986 [JP] Japan ............................. 61-130062

[51] Int. Cl.$^4$ ................................................ A61B 3/02
[52] U.S. Cl. ................................................ 351/224
[58] Field of Search ............................. 351/224-226

[56] References Cited

U.S. PATENT DOCUMENTS

| | | | |
|---|---|---|---|
| 3,172,404 | 3/1965 | Copenhauer et al. | 351/224 |
| 4,146,311 | 3/1979 | Murr | 351/226 |
| 4,169,663 | 10/1979 | Murr . | |
| 4,260,227 | 4/1981 | Munnerlyn et al. | 351/226 |

Primary Examiner—Rodney B. Bovernick
Assistant Examiner—Jay Ryan
Attorney, Agent, or Firm—Bruce L. Adams; Van C. Wilks

[57] ABSTRACT

An eye fixation monitor for ophthalmological examination is provided which is capable of automatically monitoring the eye fixation without the ophthalmologist being required to initialize the eye fixation value. The eye fixation is monitored using deviation signals derived on the basis of the eye image formed on photoelectric transducers. The eye fixation monitor is provided with means for inducing the patient to assume the eye fixation state, and to resume the monitoring automatically after the examination has been interrupted by excessive deviation of the line of sight from the eye fixation target.

8 Claims, 4 Drawing Sheets

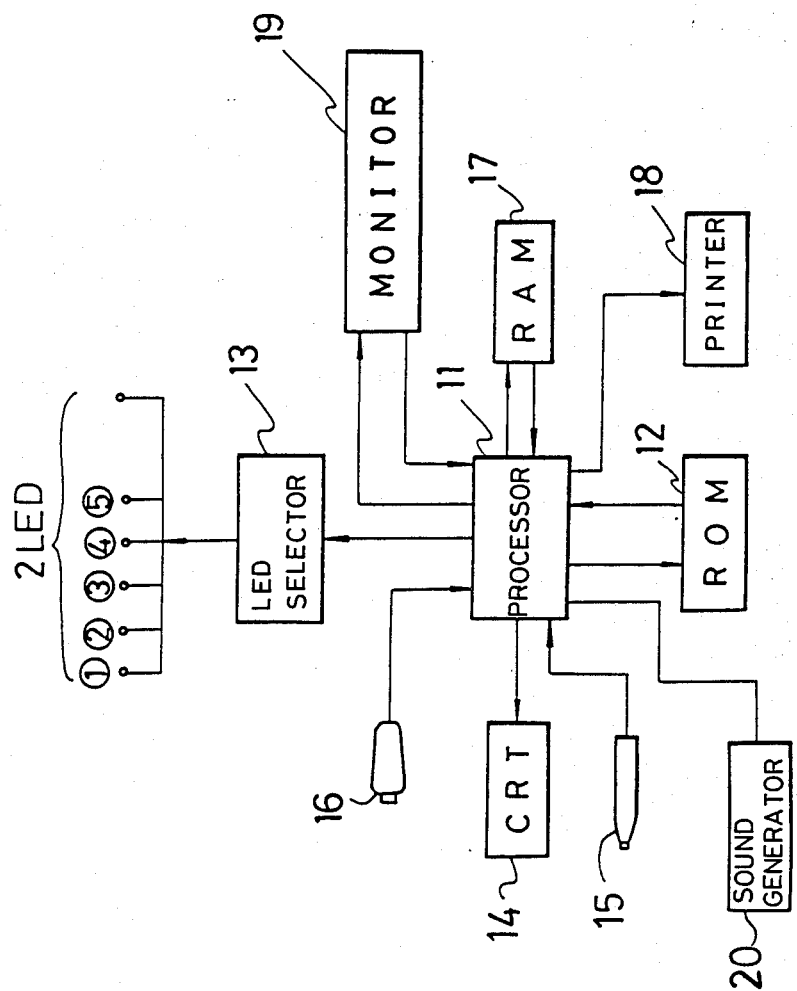

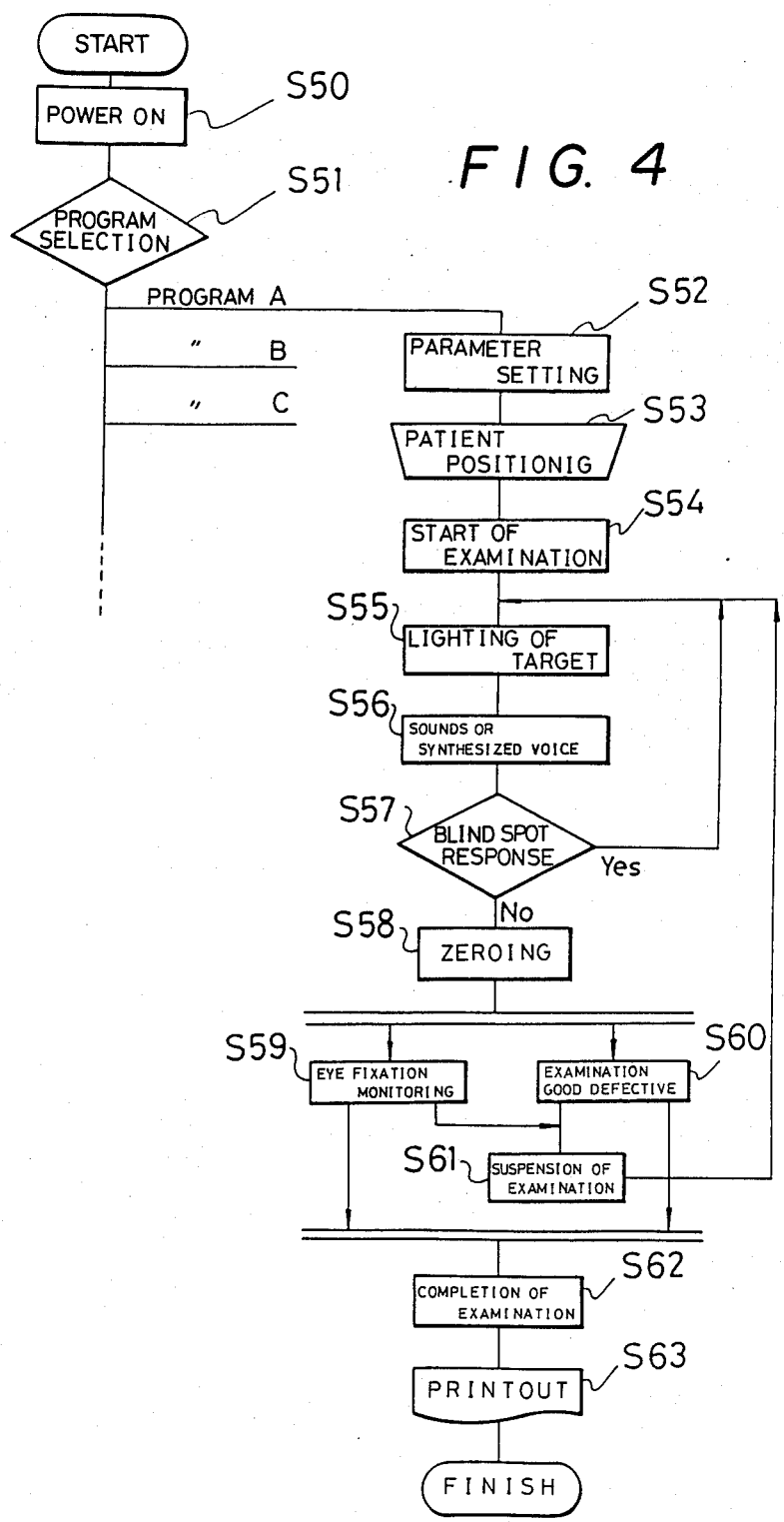

EYE FIXATION MONITOR

BACKGROUND OF THE INVENTION

1. Field of the Invention

This invention relates to an eye fixation monitor, and particularly to an eye fixation monitor for monitoring the fixation of an eye that is being examined using a perimeter or the like.

2. Description of the Prior Art

When using an ophthalmological examination apparatus such as a perimeter, it is important that during the examination the patient's line of sight is fixed on a target and for this eye fixation to be maintained for a specified period of time. The reason for this is that in the examination of a person's visual field the eye fixation target is used as the basis of reference for setting the coordinates. Therefore, if during the examination the line of sight deviates from the eye fixation target, it becomes difficult to measure the visual field.

As a method for monitoring whether the eye fixation is being maintained, there is known the method according to Japanese Laid-open Patent Application No. 60(1985)-97928, in which an optical system is used to form an image of the eye being examined, a plurality of photoelectric transducers are arranged at the position where the image is formed, a switch is provided to zero the initial value of the outputs thereof as the eye fixation state, the ophthalmologist conducting the examination operating the switch to zero the initial value while using a viewfinder or similar means to confirm the eye fixation state, following which the eye fixation is monitored.

With the aforementioned conventional type of apparatus, there are cases where the eye fixation becomes defective owing to deviation of the fixation of the patient's eye during the examination, and also in cases where the person being examined moves his face, the photoelectric transducers will function as if the eye fixation has become defective so that, notwithstanding that the patient's eye may be fixed on the target, the examination has been suspended on the grounds that the eye fixation has become defective. In such cases, it is necessary for the ophthalmologist to reconfirm the eye fixation state and operate the switch for zeroing in that state. Therefore there has been the problem that the ophthalmologist has to remain on hand by the apparatus until the completion of the examination.

SUMMARY OF THE INVENTION

It is an object of the present invention to solve the above problems by providing an eye fixation monitoring apparatus which is capable of automatically monitoring eye fixation without the ophthalmologist being required to zero the initial value in the eye fixation state.

In order to solve the above problems, the present invention comprises a means for forming eye image deviation signals in accordance with signals received from a plurality of photoelectric transducers which receive the eye image, means for monitoring the eye image fixation state in accordance with the said deviation signals, and means for inducing the patient's eye fixation state, constructed so that if during the monitoring of the eye fixation after the eye fixation state has been achieved the degree of said deviation amount exceeds a specified value, producing defective fixation, the means to induce the patient's eye fixation state is operated to resume the eye fixation monitoring.

With the present invention, when defective eye fixation occurs, the apparatus itself automatically performs a sequence of operations consisting of inducing the patient's eye fixation state, confirming this, and resuming the examination, thereby completely eliminating any need for the ophthalmologist to perform any operation pertaining to defective eye fixation occurring during the examination.

In accordance with the present invention, when the patient's eye fixation becomes defective during the examination, the apparatus itself performs the operations of prompting for the eye fixation to achieve the eye fixation state automatically and zeroing the initial value in that state, thereby removing the need with the conventional apparatus for the ophthalmologist to be at the apparatus throughout the examination, and as such the burden on the ophthalmologist is lightened as a result of the decrease in the amount of time the ophthalmologist is tied up.

BRIEF DESCRIPTION OF THE DRAWINGS

The purposes and features of the present invention will become more apparent from a consideration of the following detailed description taken in conjunction with the accompanying drawings in which:

FIG. 3 is a block diagram of the eye fixation monitor incorporating a computer; and FIG. 4 is a flowchart of the control sequence of the perimeter used with the eye fixation monitor according to the present invention.

DETAILED DESCRIPTION OF THE PREFERRED EMBODIMENT

Figure 1:
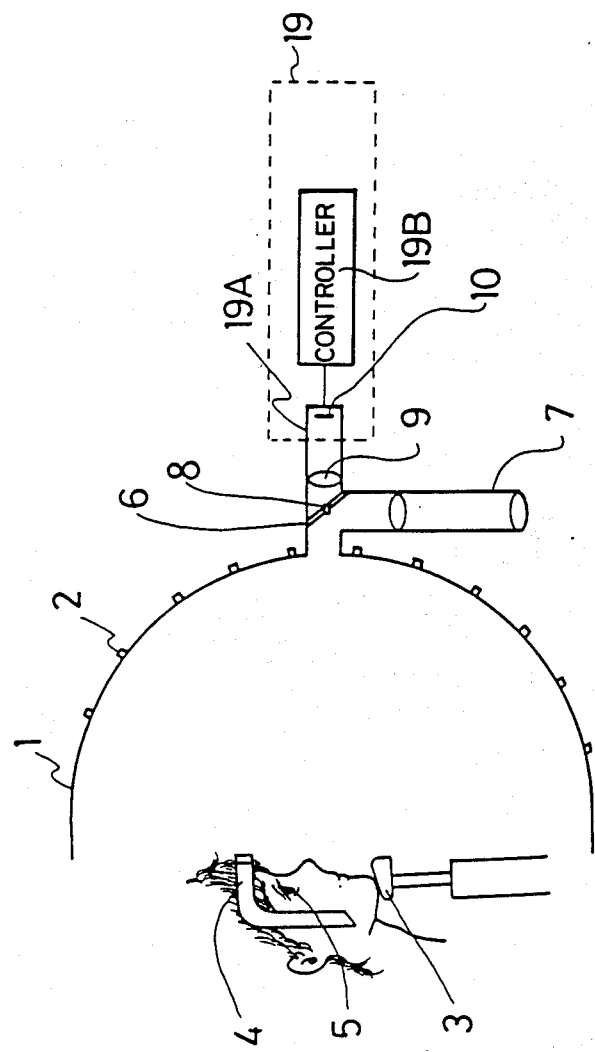
FIG. 1 is an outline block diagram showing the eye fixation monitor of the present invention combined with a perimeter.

This invention is described in detail below on the basis of the preferred embodiments illustrated in the drawings.

With reference to FIG. 1 which shows an outline of the eye fixation monitor of the present invention combined with a perimeter, the numeral 1 denotes the dome of the perimeter. On the dome 1 are distributed a plurality of LEDs (light-emitting diodes) 2 which serve as a target for the line of sight of the patient. A chin-rest 3 is affixed at a position opposite the dome 1 for the patient's chin to rest on during examination of the visual field, and a corresponding headrest 4 is provided to fix the position of the patient's face.

The eye 5 is examined by the ophthalmologist by means of a half-mirror 6 and a viewfinder 7. The gaze of the eye 5 is made to fix onto the target 8 and the chin-rest 3 and the headrest 4 are adjusted (not shown) to set the eye 5 at the correct position. The image of the eye 5 is formed via a lens 9 on a plurality (preferably four) of photoelectric transducers 10 set closely together in a flat plane.

The eye fixation mounting unit 19 monitors the movement of the image formed on the photoelectric transducers 10, using the outputs of the photoelectric transducer, and consists of an eye fixation monitoring detector section 19A which is comprised of the photoelectric transducers 10, and an eye fixation monitoring control circuit 19B.

Figure 2:
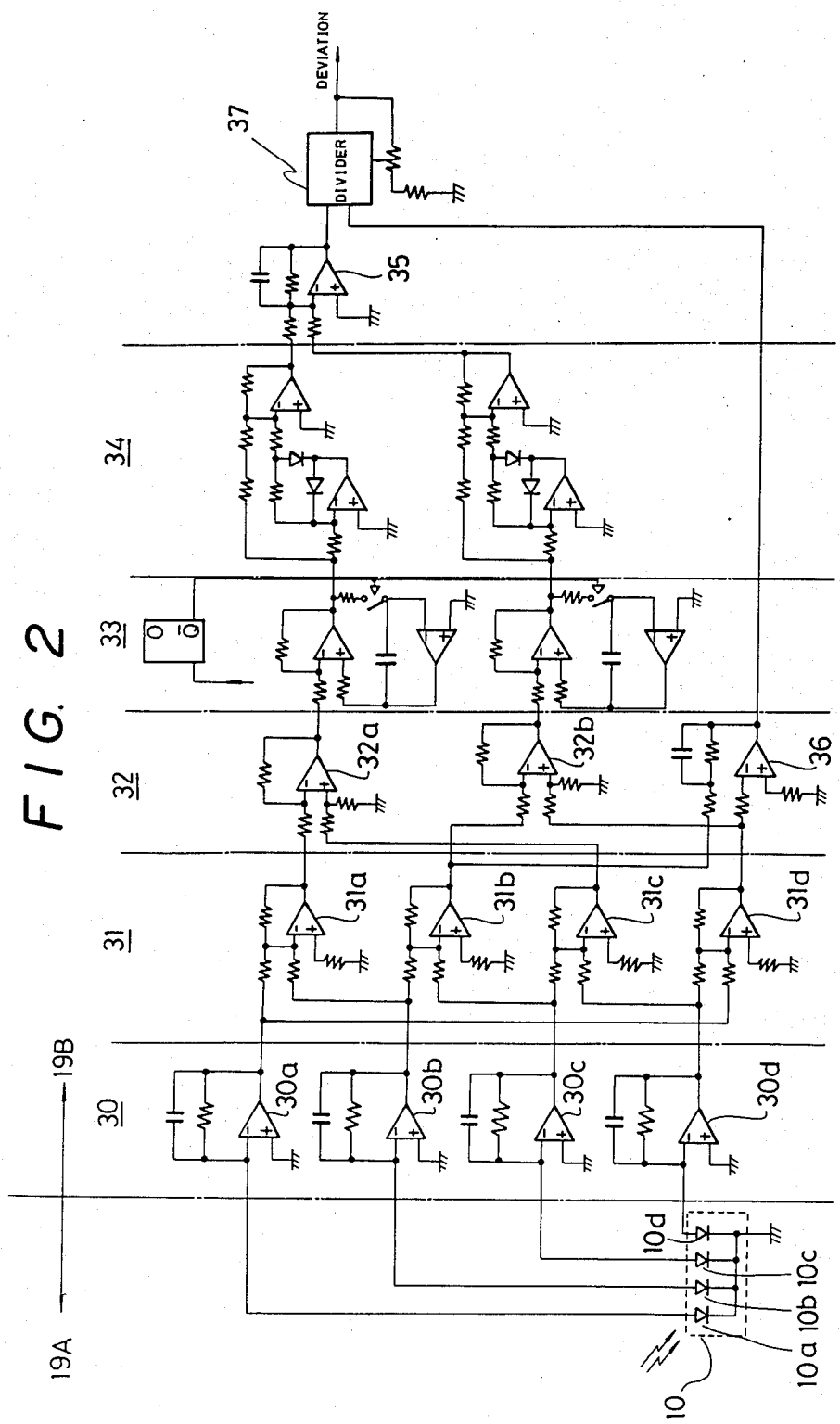
FIG. 2 is a circuit diagram of the eye fixation monitor unit.

With reference to FIG. 2 which shows details of the eye fixation unit 19, the plurality of photoelectric transducers 10 is made up of four photoelectric transducers 10a to 10d on which is formed the image of the eye being examined. The photoelectric transducers 10a to 10d are arranged in a close vertical and horizontal interrelationship so that the tangential lines thereof lie in the X and Y directions.

The photoelectric transducers 10a to 10d are connected to an amplifier section 30 with corresponding preamplifiers 30a to 30d. The outputs of the preamplifiers 30a and 30b are connected to an adder 31a; the outputs of the preamplifiers 30b and 30c are connected to an adder 31b; the outputs of the preamplifiers 30c and 30d are connected to an adder 31c; and the outputs of the preamplifiers 30d and 30a are connected to an adder 31d. The outputs of adjacent preamplifiers 30a to 30d are thereby added in adder section 31 by the adders 31a to 31d. The adders 31a to 31d cancel the mean value (offset light) of the preamplifiers 30a to 30d.

The outputs of the adders 31a and 31c are connected to a subtracter 32a; the outputs of the adders 31b and 31d are connected to a subtracter 32b; and the outputs of the adders 31b and 31d are input to an adder 36. The sums $(10a+10b)$, $(10c+10d)$ and the differences $(10b+10c)$, $(10d+10a)$ of the outputs of adjacently opposed photoelectric transducers are obtained by the subtracter 32 which consists of subtracters 32a and 32b. The sum total for the photoelectric transducers 10a to 10d is obtained by the adder 36. The output of the subtracter 32 is connected to an initial value zeroing holding circuit 33 which, in turn, is connected via an absolute value circuit 34 to an adder 35, the output of which is connected to a divider 37. The output of the adder 36 is input to the divider 37 which performs division on the outputs from the adders 36 and 35, and the output from the divider 37 is output as an eye fixation state monitoring deviation signal.

With the above arrangement, the signals output from the photoelectric transducers 10a to 10d are amplified by the corresponding preamplifiers 30a to 30d and then the outputs of adjacent photoelectric transducers are added by the adders 31a to 31d. Following this, the outputs thus added are subtracted by the subtracters 32a and 32b, subtraction being performed with respect to each opposed set, i.e., with respect to the X and Y directions. The output of the subtracter 32 is input to the initial value zeroing holding circuit 33 to thereby hold the initial value at zero in order to provide a basis of reference for differences in output in the eye fixation state. Deviation in the eye fixation will destroy the balance, an output being produced in accordance with the amount of deviation. The output produced here accompanying deviation in the X and Y directions is given the same sign in the absolute value circuit 34, then added in the adder 35 and the sum of the deviation output is output. The sum total of the outputs of the photoelectric transducers is calculated in the adder 36, so by the division in the divider 37 of the sum of the deviation amount outputs by the sum total of the photoelectric transducers, a deviation signal is derived as an eye fixation monitoring signal. By means of this divider circuit, sensitivity with respect to the amount of eye movement can be maintained constant even when the level of eye illumination is changed.

As shown in FIG. 3, the eye fixation monitoring unit 19, thus constructed, inputs to the microprocessor 11, effecting control of the present invention.

The requisite program for the examination is stored in a ROM 12. The ROM 12 is connected to the microprocessor 11, and also connected to the microprocessor 11 are a light-pen 15, a CRT 14 and a response switch 16, and via an LED selector 13 the plurality of LEDs 2 arranged on the dome 1 are lighted in a specified sequence. Also connected to the microprocessor 11 is a RAM 17 in which specified results are stored and output to a printer 18 via the microprocessor 11. Also connected to the microprocessor 11 is the aforementioned eye fixation monitoring unit 19 which detects whether or not the state of eye fixation of the eye 5 is being maintained. A sound generator 20 also connected to the microprocessor 11 which can warn the patient by sounds or synthesized voice if the patient's eye fixation deviates.

The operation of the apparatus of the invention thus constructed will now be explained with reference to FIG. 4.

First, the power is switched on in step S50, program selection is performed in step S51 and parameters are set in step S52. Specifically, the brightness of the LEDs2, the background rightness, the length of time the LEDs are lit and the periods between the lighting and the like are set.

Next, the patient is positioned in the specified position and adjustments are performed to bring the eye to be examined to the correct position (step S53). In step S54 the examination is started, and in order to zero the initial value as the eye fixation state, in step S55 the target 8 is made to flash on, and in step S56 the patient is prompted to provide the eye fixation by sounds or synthesized voice generated by the sound generator 20. In step S57 the LED in the position corresponding to the blind spot is lighted, and if there is a response it is determined that the eye fixation is defective and steps S55 to S57 are repeated. In step S57, if there is no response it is determined that eye fixation is good, and the initial value is zeroed (step S58). Following this, while the eye fixation is being monitored (step S59) the examination is performed (step S60). If the eye fixation becomes defective during the examination, the examination is suspended (step S61), the processing of the steps S55 to S58 is performed and examination is again conducted (step S60) while the eye fixation is being monitored (step S59). When all the examination points in the program have been checked, the examination is finished (step S62).

The contents of the program are displayed on a CRT 14; any changes that need to be made to the parameters, for example, are input by means of the light-pen 15. When the examination starts, the microprocessor 11 indicates the addresses of the LEDs 2 in accordance with the program stored in the ROM 12, and in accordance with these indications the LED selector 13 lights the LEDs on the dome 1. When the patient keeping his eye fixed on the target 8 located at the center of the dome 1 confirms that a LED 2 has lighted, the response switch 16 is pressed to perform the visual field examination.

If during the examination the patient's eye fixation becomes defective, movement will occur of the eye image formed on the plurality of photoelectric transducers 10 and the output of the photoelectric transducers will vary, and if the variation exceeds by more than a specified permissible value the initial value zeroed as the eye fixation state in the eye fixation monitoring control circuit 19B, it is determined that the eye fixation is defective. In the event of the eye fixation becoming defective, as already described in the above the prompting of the patient for eye fixation is carried out (steps S55 to S57) and on the basis of commands from the microprocessor 11 the initial value is again zeroed in the eye fixation monitoring unit 19 and the examination is resumed.

The results of the examination are stored in the RAM 17 and can be output onto a record sheet by the printer 18.

In this embodiment, when the fixation of the eye has become defective, refixation can be aided by such methods as lighting the target, providing warning sounds or synthesized-voice warnings, and ascertaining the presence or absence of a blind-spot response. These can be combined or reordered as desired, and it is not, of course, required to use all of them.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An eye fixation monitor comprising: a plurality of photoelectric transducers receptive of an image of an eye thereon for producing signals corresponding thereto; means for producing a deviation signal corresponding to the movement of the eye which is imaged on the transducers; and means for producing a signal when the deviation signal exceeds a predetermined value, the means for producing the deviation signal comprising first adder means for adding the signals from each two adjacent transducers, subtracter means for subtracting the outputs from the adders to obtain subtracted outputs, the subtractor means including an initial value zeroing holding circuit receptive of the initial output of the subtractor means to provide a reference value when the eye to be examined is in a fixation state reference position, secondadder means for summing the outputs of all of the first adder means, third adder means for summing the outputs from the subtractor means to obtain a signal corresponding to a deviation of the image of the eye from the reference position and divider means for dividing the output of the third adder means by the output of the second adder means to produce the deviation signal.

2. The eye fixation monitor according to claim 1; further comprising means for inducing a person being examined to enter an eye fixation state when the first signal is produced.

3. The eye fixation monitor according to claim 2; wherein transducer signals corresponding to the eye fixation state are stored in a memory.

4. The eye fixation monitor according to claim 2; wherein said means for inducing the person being examined to enter the eye fixation state comprises flashing means.

5. The eye fixation monitor according to claim 2; wherein said means for inducing the person being examined to enter the eye fixation state comprises a warning device.

6. The eye fixation monitor according to claim 1; wherein said means for inducing the person being examined to enter the eye fixation state comprises means for applying a stimulus at a position corresponding to a blind spot of the person.

7. The eye fixation monitor according to claim 7; wherein the subtractor means further comprises means for subtracting reference values from the outputs of the subtracter means to obtain deviation outputs, means for obtaining the absolute value of the deviation outputs and means for applying the absolute values of the deviation outputs to the third adder means for the summing therein.

8. The eye fixation monitor according to claim 1; wherein the subtractor means subtracts the outputs of the sums of transducers in opposed sets corresponding to X and Y orthogonal axes.

* * * * *